US011815639B2

United States Patent
Ye et al.

(10) Patent No.: US 11,815,639 B2
(45) Date of Patent: Nov. 14, 2023

(54) BOREHOLE FLUID GEL STRENGTH MEASUREMENT

(71) Applicant: Halliburton Energy Services, Inc., Houston, TX (US)

(72) Inventors: Xiangnan (Allan) Ye, Cypress, TX (US); Dale E. Jamison, Atascocita, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 683 days.

(21) Appl. No.: 16/670,560

(22) Filed: Oct. 31, 2019

(65) Prior Publication Data

US 2021/0132243 A1 May 6, 2021

(51) Int. Cl.
| | |
|---|---|
| *G01V 1/133* | (2006.01) |
| *G01V 1/02* | (2006.01) |
| *C09K 8/32* | (2006.01) |
| *G01V 11/00* | (2006.01) |

(52) U.S. Cl.
CPC ............... *G01V 1/133* (2013.01); *C09K 8/32* (2013.01); *G01V 1/159* (2013.01); *G01V 11/005* (2013.01)

(58) Field of Classification Search
CPC .......... G01V 1/133; G01V 1/159; C09K 8/32; C09K 8/02; G01N 33/2823; G01N 11/00
See application file for complete search history.

(56) References Cited

U.S. PATENT DOCUMENTS

| | | | | |
|---|---|---|---|---|
| 4,579,667 | A * | 4/1986 | Echt | C09K 8/68 |
| | | | | 523/411 |
| 5,047,456 | A * | 9/1991 | Onwumere | C08G 85/00 |
| | | | | 528/65 |
| 5,253,513 | A | 10/1993 | Van | |
| 6,194,356 | B1 | 2/2001 | Jones | |
| 7,287,415 | B2 | 10/2007 | Borwick | |
| 8,653,321 | B2 * | 2/2014 | Lindner | G01N 11/165 |
| | | | | 428/327 |

(Continued)

OTHER PUBLICATIONS

Rubens R. Fernandes, et al., "Correlation between the gel-liquid transition stress and the storage modulus of an oil-based drilling fluid", Journal of Non-Newtonian Fluid Mechanics, vol. 231, pp. 6-10 (Year: 2016).*

(Continued)

*Primary Examiner* — Ian J Lobo
(74) *Attorney, Agent, or Firm* — K&L Gates LLP

(57) ABSTRACT

A method and systems for performing a borehole operation with a borehole fluid that includes applying an amplitude oscillation deformation force to a sample of the borehole fluid over a period of time, measuring the deformation force from the sample, determining a storage modulus of the borehole fluid over the period of time based on the measured deformation force, determining a gel strength of the borehole fluid by correlation with the storage modulus, comparing the gel strength with a desired gel strength and if the gel strength is outside of an acceptable range of the desired gel strength, adjusting a drilling parameter, a composition of the borehole fluid, or a combination thereof, and using the borehole fluid in the borehole operation. Determining the storage modulus and the gel strength may be done using a processor and the force may be applied using a piezoelectric device.

20 Claims, 6 Drawing Sheets

(56) References Cited

U.S. PATENT DOCUMENTS

2013/0157956 A1* 6/2013 Kluijtmans ............ A61L 27/26
514/17.2
2013/0226473 A1 8/2013 Murphy
2017/0276584 A1 9/2017 Ye
2019/0055460 A1* 2/2019 Mohammed ............ C09K 8/32

OTHER PUBLICATIONS

Ye, Allan, et al., "Gel Strength Measurement for Drilling Fluid: Reform of Gel Microstructure", AADE-15-NTCE-4 (American Associate of Drilling Engineers), National Technical Conference, Apr. 8-9, 2015, San Antonio, TX, pp. 1-5.
Koven, Robert, et al., "Low-Frequency and Broadband Vibration Energy Harvesting Using Base-Mounted Piezoelectric Transducers", IIEE Transactions on Ultrasonics, Ferroelectrics, and Frequency Control, vol. 64, No. 11, Nov. 2017, pp. 1735-1743.

* cited by examiner

BOREHOLE FLUID GEL STRENGTH MEASUREMENT

BACKGROUND

This section is intended to provide relevant background information to facilitate a better understanding of the various aspects of the described embodiments. Accordingly, it should be understood that these statements are to be read in this light and not as admissions of prior art.

Borehole fluids are often used to aid in borehole operations such as the drilling of boreholes into subterranean formations. For example, treatment fluids are fluids designed and prepared to resolve a specific borehole or reservoir condition. Treatment fluids can be prepared at the wellsite and can be used for a wide range of purposes, such as stimulation, isolation, or control of reservoir gas or water. Every treatment fluid is intended for specific conditions and should be prepared and used as directed to ensure reliable and predictable performance.

Treatment fluids include fracturing fluids, which are fluids injected into a well as part of a stimulation operation. Fracturing fluids for shale reservoirs usually contain water, proppant, and nonaqueous fluids designed to reduce friction pressure while pumping the fluid into the borehole. These fluids may include additives such as gels, friction reducers, crosslinkers, breakers, and surfactants selected for their capability to improve the results of the stimulation operation and the productivity of the well.

Treatment fluids also include workover fluids, which are well-control fluids, e.g., a brine, used during workover operations. Since the borehole is in contact with the reservoir during most workover operations, workover fluids should be clean and chemically compatible with the reservoir fluids and formation matrix.

Another example of a borehole fluid is drilling fluid that aids to remove cuttings from the borehole, control formation pressure, and cool, lubricate and support the bit and drilling assembly. Typically, the drilling fluid, which is more commonly referred to as "drilling mud" or "mud," is pumped down the borehole through the interior of the drill string, out through nozzles in the end of the bit, and then upwardly in the annulus between the drill string and the wall of the borehole. During the ascent, some of the mud congeals, forming a cake on the exposed face of the borehole, for example, to prevent the mud from being lost to the porous drilled formation. In addition, the pressure inside the formation can be partially or fully counterbalanced by the hydrostatic weight of the mud column in the borehole. Since the mud has a variety of vital drilling functions, it must accordingly have comparable and reliable capabilities. In the oil and gas industry, it can be important to precisely determine the characteristics and chemical compositions of drilling fluids circulating into and out of subterranean hydrocarbon-bearing formations. However, drilling fluids are often circulated through the borehole several times where the drill cuttings, leak-off, and the like can change the composition of the drilling fluid.

Many drilling parameters, such as measured depth, string rotary speed, weight on bit, downhole torque, surface torque, flow in, surface pressure, downhole pressure, bit orientation, bit deflection, and the like, can be made available in real-time. However, the composition of the drilling fluid, which impacts effective hydraulic modeling and hole cleaning performance, is not readily available in real-time. Ascertaining the composition of the drilling fluid usually requires a direct measurement by a technician (or "mud engineer").

The on-site mud engineer, for example, typically has numerous other responsibilities in his/her daily routine and, therefore, cannot provide a constant stream of drilling fluid composition to a monitoring center. In addition, taking and/or generating such measurements is time consuming and inherently susceptible to human error.

For fluids, gel strength is a measurement of the ability of the fluid to develop and retain a gel structure. With drilling fluids, for example, gel strength is monitored during drilling operations. The drilling fluids by nature show thixotropy behavior, in which the gel strength is a time dependent rheological property. Gel structure is eventually developed as soon as the drilling fluids stop deforming/flowing.

Traditional measurements for gel strength are performed on FANN®, 35, RHEOVADR®, AMETEK® Brookfield viscometer, etc. using 10 second, 10 minute, and 30 minute gelation times, which would be used for modeling the drilling fluid's hydraulics performance during pump-up and tripping operations. The measurement is a time consuming process. Also, the gel strength at a gelation time other than at these three time values is calculated by extrapolation, which introduces uncertainty into hydraulic models. Automation with the mechanical design difficulty is also a challenging using the bob/cup measurement of a traditional viscometer.

DESCRIPTION OF THE DRAWINGS

Embodiments of the methods and systems for borehole fluid gel strength measurement are described with reference to the following figures. The same numbers are used throughout the figures to reference like features and components. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

The present disclosure provides for borehole fluid gel strength measurement that includes applying an amplitude oscillation deformation force to a sample the borehole fluid over a period of time. By doing so, the formation of micro gelation within the borehole fluid may be monitored. The storage modulus, G', the ability of the borehole fluid to maintain or store energy upon deformation, has a correlation to the gel strength. Thus, the gel strength of the borehole fluid may be measured with instrumentation at or near a system at a wellsite. Then, the gel strength may be used to characterize the borehole fluid, which may then be altered as needed to improve the performance of the borehole fluid and the efficiency of the borehole operation. In the alternative or in addition to altering the borehole fluid, the parameters of the borehole operation may be altered to adjust for the gel strength of the borehole fluid.

Unless otherwise specified, the term "borehole fluid" can be any type of fluid used in the drilling of a borehole or the treatment of a formation through the borehole. Examples of such fluids include, drilling fluids, treatment fluids, fracturing fluids, workover fluids.

Figure 1:
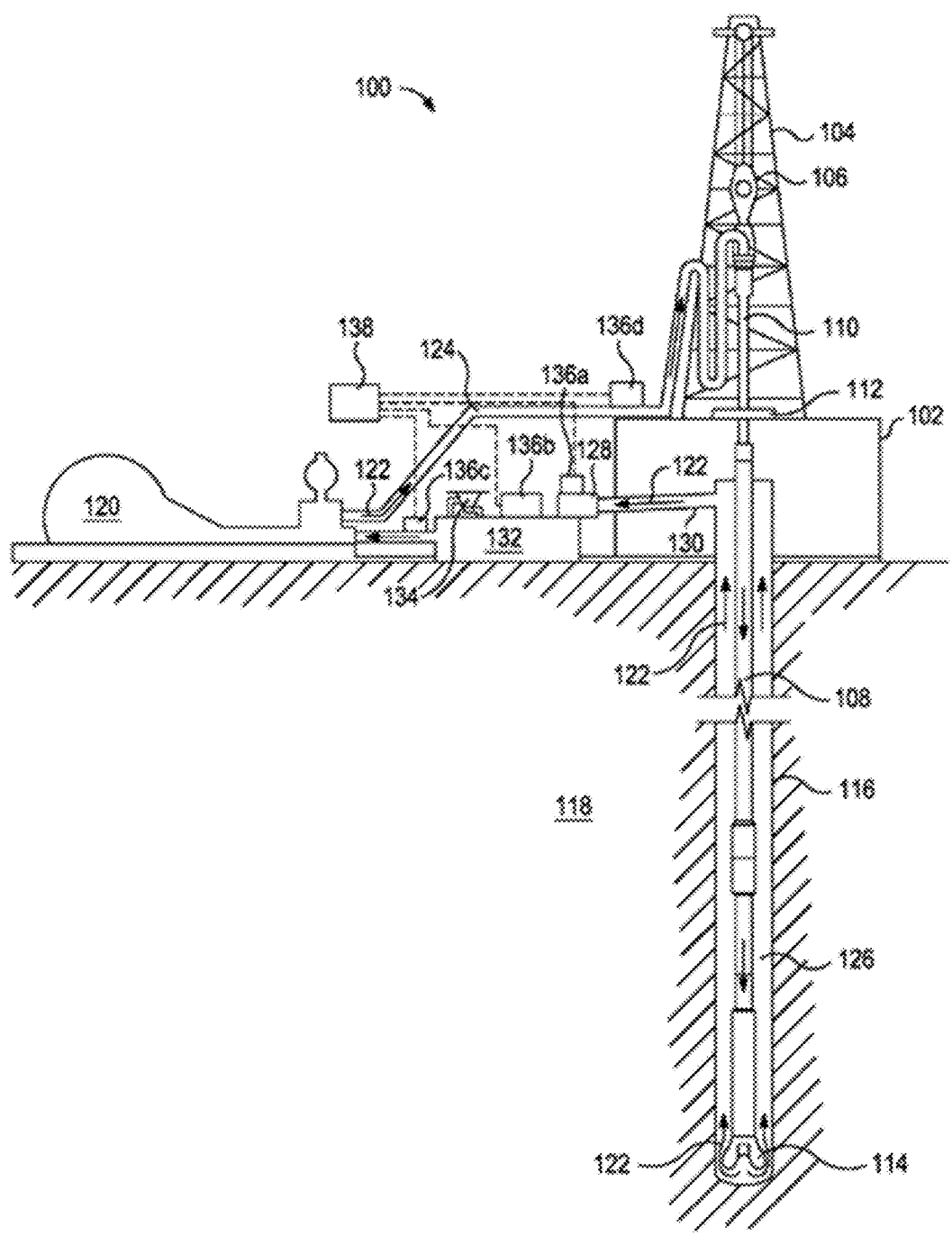
FIG. 1 is a schematic diagram of an embodiment of a borehole drilling system.

FIG. 1 is an embodiment of a borehole drilling system 100. It should be noted that while FIG. 1 generally depicts a land-based drilling assembly, those skilled in the art will recognize that the principles described herein are equally applicable to subsea drilling operations that employ offshore floating or sea-based platforms and rigs, without departing from the scope of the disclosure. While FIG. 1 depicts a drilling system 100 that uses a borehole fluid in the nature of a drilling fluid, FIG. 1 is meant to depict an example of use of a type of borehole fluid. Those skilled in the art will readily recognize that the principles described herein are equally applicable to other types of borehole operations and other types of borehole fluids discussed above.

As illustrated, the drilling system 100 includes a drilling platform 102 that supports a derrick 104 having a traveling block 106 for raising and lowering a drill string 108. The drill string 108 includes, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the drill bit 114 rotates, it creates a borehole 116 that penetrates various subterranean formations 118.

A pump 120 (e.g., a mud pump) circulates a borehole fluid 122, e.g., drilling fluid, through a feed pipe 124 and to the kelly 110, which conveys the borehole fluid 122 downhole through the interior of the drill string 108 and through one or more orifices in the drill bit 114. The borehole fluid 122 is then circulated back to the surface via an annulus 126 defined between the drill string 108 and the walls of the borehole 116. At the surface, the recirculated or spent borehole fluid 122 exits the annulus 126 and may be conveyed to various surface treatment systems (e.g., fluid processing units, retention pits, mixers, and the like). As illustrated, the spent borehole fluid 122 is conveyed to a fluid processing unit 128 via an interconnecting flow line 130. Generally, the fluid processing unit 128 cleans the borehole fluid, for example, by removing drill cuttings brought to the surface. The fluid processing unit 128 may include one or more of: a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment, and the like, and any combination thereof. The fluid processing unit 128 may further include one or more sensors, gauges, pumps, compressors, and the like.

After passing through the fluid processing unit 128, a "cleaned" borehole fluid 122 is deposited into a nearby retention pit 132 (i.e., a mud pit). While illustrated as being arranged at the outlet of the borehole 116 via the annulus 126, those skilled in the art will appreciate that the fluid processing unit 128 and retention pit 132 may be arranged at any other location in the drilling system 100 to facilitate its proper function, without departing from the scope of the disclosure.

Components of the borehole fluid 122 (e.g., weighting agents and fluid loss control additives) may be added to the borehole fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the borehole fluid components may be added to the borehole fluid 122 at any other location in the drilling system 100. In at least one embodiment, for example, there could be more than one retention pit 132, such as multiple retention pits 132 in series. Moreover, the retention pit 132 may be representative of one or more fluid storage facilities and/or units where the borehole fluid components may be stored, reconditioned, and/or regulated until added to the borehole fluid 122.

While not illustrated, the drilling system 100 may further include additional downhole equipment and tools that such as, but not limited to, floats, drill collars, mud motors, downhole motors and/or pumps associated with the drill string 108, and any measurement-while-drilling or logging-while-drilling (MWD/LWD) tools and related telemetry equipment, and sensors or distributed sensors associated with the drill string 108.

The drilling system 100 also includes an analysis system 136 (illustrated as three analysis systems 136 a-d) communicably coupled to a control system 138 so that the control system 138 received measurements and/or data collected by the analysis system 136. The analysis system 136 and the control system 138 may be co-located or physically separated in the drilling system 100. There may also be less or more than three analysis systems 136. Additional, the analysis system 136 may be in-line so as to be able to sample directly from the flow of the borehole fluid through the drilling system 100.

The analysis system 136 is configured and operable to test samples from the borehole fluid and measure the sample's gel strength. As shown, the illustrated drilling system 100 includes four analysis systems 136 with a first analysis system 136a fluidly coupled to the fluid processing unit 128, a second analysis system 136b fluidly coupled to the retention pit 132, a third analysis system 136c fluidly coupled to a tubular after the retention pit 132 and the mixing hopper 134, and a fourth analysis system 136d coupled to the feed pipe 124 before the borehole fluid 122 is introduced back into the drill string 108. The analysis systems 136 described herein may be placed at one or more of the foregoing locations or at other locations along the borehole fluid flow path of the drilling system 100 depending on the processing stage of the borehole fluid for testing. For example, the placement of the third and fourth analysis systems 136c,d may be useful in providing real-time measurements of the properties of the borehole fluid 122 being placed downhole, which allows for adjusting parameters of the drilling operation (e.g., weight-on-bit, borehole fluid flow rate, or drill bit rotation speed) to optimize or increase the efficiency and efficacy of the drilling operation. More on the analysis system 136 is described below.

The control system 138 and corresponding computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. The computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

The control system 138 described herein is configured for receiving inputs from the analysis system 136. The processor may also be configured to perform or reference mathematical calculations, lookup tables, and offset well data comparisons that are stored on the processor to derive the gel strength. In some instances, the processor may output a numerical value, graph, or the like indicative of the gel strength. In some instances, the processor may change or suggest a change to the borehole fluid composition (e.g., adding additional fluid components), the drilling operation parameters (e.g., increasing or decreasing the rate of penetration and weight on bit), or both based on the derived gel strength.

The drilling system 100 may further comprise other sensors that are communicably coupled to the control system 138. These sensors may provide real-time measurements of the oil-to-water ratio of the borehole fluid, the density of the borehole fluid, the rheology of the borehole fluid (e.g., the shear stress, the yield stress, the viscosity, the shear-thinning index, and the like), and the like, and any combination thereof. These real-time measurements may optionally be used in combination with the gel strength when the processor makes a change or suggests a change to the borehole fluid composition (e.g., adding additional weighting agent), the borehole operation parameters (e.g., increasing or decreasing the rate of penetration and weight on bit), or both.

Figure 2A:
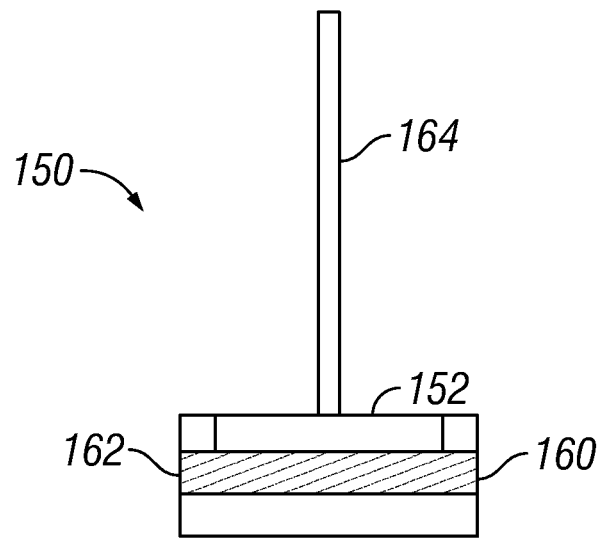
FIGS. 2A-C are schematic diagrams of a first embodiment of a rheometer of an analysis system.
Figure 2B:
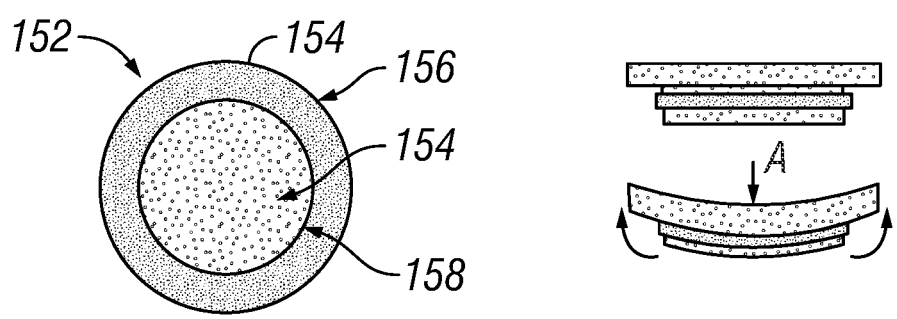
Figure 2C:
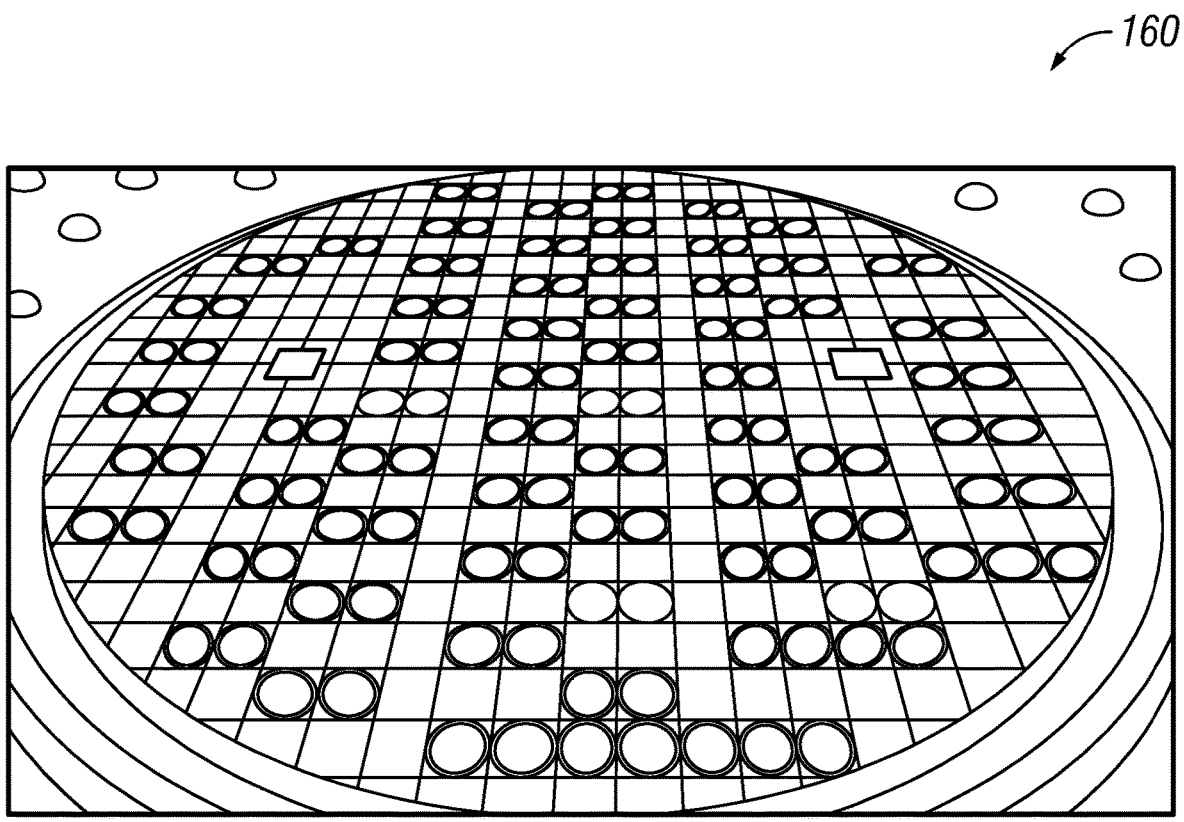

One or more of the analysis systems 136*a-d* include a rheometer operable to determine the gel strength of the borehole fluid. FIGS. 2A-C illustrate an embodiment of a rheometer 150 as used in the analysis system(s) 136. As illustrated the rheometer 150 includes a piezoelectric device 152 spaced from a dynamic pressure sensor 160 such that a borehole fluid sample 162 may be placed between for testing.

As shown in more detail in FIG. 2B, the piezoelectric device 152 may be any suitable piezoelectric device for imparting a force A in response to an electric current applied across the piezoelectric device 152. Adjusting the electric current flowing through the piezoelectric device 152 controls the amplitude and frequency of the force A applied to the borehole fluid sample 162 in the direction A as shown. To impart force at a controlled oscillation, the piezoelectric device 152 includes, for example, a piezo material disc 158 surrounded by a metal plate 156. The piezo material disc 158 and the metal plate 156 are electrodes 154 and complete an electric circuit using electrical conduits (not shown). An electric current is applied through the piezoelectric device 152 so as to alter the physical shape of the piezoelectric device 152 as shown in FIG. 2B and impart a force A to the borehole fluid sample 162 in a direction generally toward the dynamic pressure sensor 160. Such direction may be described as a linear or normal force. Most commercial piezo products have a resonant frequency in the order of 1,000 Hz, which is too high for the amplitude oscillation deformation test performed with this device (described below). The piezo material circuit therefore is modified or designed for generating low frequency vibration such as 0.1-50 Hz, as is known by those skilled in the art.

The force received though, or from, the borehole fluid sample 162 as a result of the force A is measured by a dynamic pressure sensor 160. The dynamic pressure sensor 160 may be any suitable sensor for measuring the pressure from the borehole fluid sample 162 that results from the force A from the piezoelectric device 152. The pressure sensor 160 may also be selected to have an appropriate measurement range. As an example, the pressure sensor 160 may have a measurement range of 0-50 Pa. With the surface area known and the pressure measured, the force from the borehole fluid sample 162 can then be calculated.

In operation, a borehole fluid sample 162 is tested using one or more of the analysis systems 136 in communication with the control system 138. As an example, the borehole operation may be a borehole drilling operation using the borehole drilling system 100 as shown in FIG. 1 and the borehole fluid 122 may be drilling fluid. However, it is apparent to those of skill in the art that other borehole operations may also be performed and other borehole fluids tested. Before or even during the borehole operation, a borehole fluid sample 162 is placed in at least one of the analysis systems 136*a-d*, and more specifically, the borehole fluid sample 162 is placed between the piezoelectric device 152 and the dynamic pressure sensor 160. Although FIG. 2A shows a layer of the borehole fluid sample 162, no specific amount of borehole fluid 122 needs to be sampled for testing. The borehole fluid may be tested "in-line" with the fluid flow or a sample may be pulled from the fluid flowpath and tested separately.

Once the borehole fluid sample 162 is in place, the control system 138 operates the analysis system 136 by controlling an electric current through the piezoelectric device 152 in an oscillating manner, thus applying an amplitude oscillation deformation force to the borehole fluid sample 162 over a period of time by oscillating the amplitude of the force A created by the piezoelectric device 152. As noted above, the frequency of the oscillations are in the range of 0.1-50 Hz and is maintained throughout the testing.

The amplitude oscillation deformation force may also be at such a frequency and amplitude as to impart a vibration to the borehole fluid sample 162. Further, the amplitude oscillation deformation force may be applied to the borehole fluid sample 162 over a period of time that is the gellation period of time for the borehole fluid 122. The amplitude oscillation deformation force may also be applied continuously over the period of time of the testing or intermittently depending on the parameters of the testing protocol. The force A applied to the borehole fluid sample 162 is such that the deformation can be fully recovered upon removal of the force A and as used herein is considered a "small amplitude." The small amplitude stress is introduced to the borehole fluid so as to deform the borehole fluid but remain within the viscoelastic regime, which means it is not enough to damage the fluid structure. The amplitude of the force A created from the piezoelectric device 152 is thus maintained within the linear viscoelastic strain limit of the borehole fluid sample 162. For example, for a drilling fluid, the linear viscoelastic strain limit is typically 5-10% and the force A could be kept constant at 5%. The force is measured from the borehole fluid sample 162 during the deformation and as an example, the measured force may reach a maximum amount of 50 Pa.

The dynamic pressure sensor 160 measures the force applied from the piezoelectric device 152 through the borehole fluid sample 162 and sends the measurement information to the control system 138 for determining the storage modulus of the borehole fluid sample 162 over time. To do so, the amplitude defined from the piezoelectric device 152 can be written as:

$$\gamma = \gamma_0 \sin(\omega t) \quad \text{(Equation 1)}$$

where $\omega$ is the frequency. The borehole fluid sample 162 response to this deformation can be written in terms of stress as:

$$\tau = \tau_0 \sin(\omega t + \delta) = G'(\omega)\sin(\omega t) + G''(\omega)\cos(\omega t) \quad \text{(Equation 2)}$$

where $\delta$ is the phase lag, characterized by the borehole fluid sample's 162 viscoelastic property. G' and G" are storage and loss moduli respectively. Further, $$\tau = \tau_0 \sin(\omega t + \delta) = \tau_0[\sin(\omega t)\cos(\delta) + \sin(\delta)\cos(\omega t)] = G'(\omega)\sin(\omega t) + G''(\omega)\cos(\omega t) \quad \text{(Equation 3)}$$

Thus, $$G'(\omega) = \tau_0 \cos(\delta) \quad \text{(Equation 4)}$$

and $$G''(\omega) = \tau_0 \sin(\delta) \quad \text{(Equation 5)}$$

Figure 3:
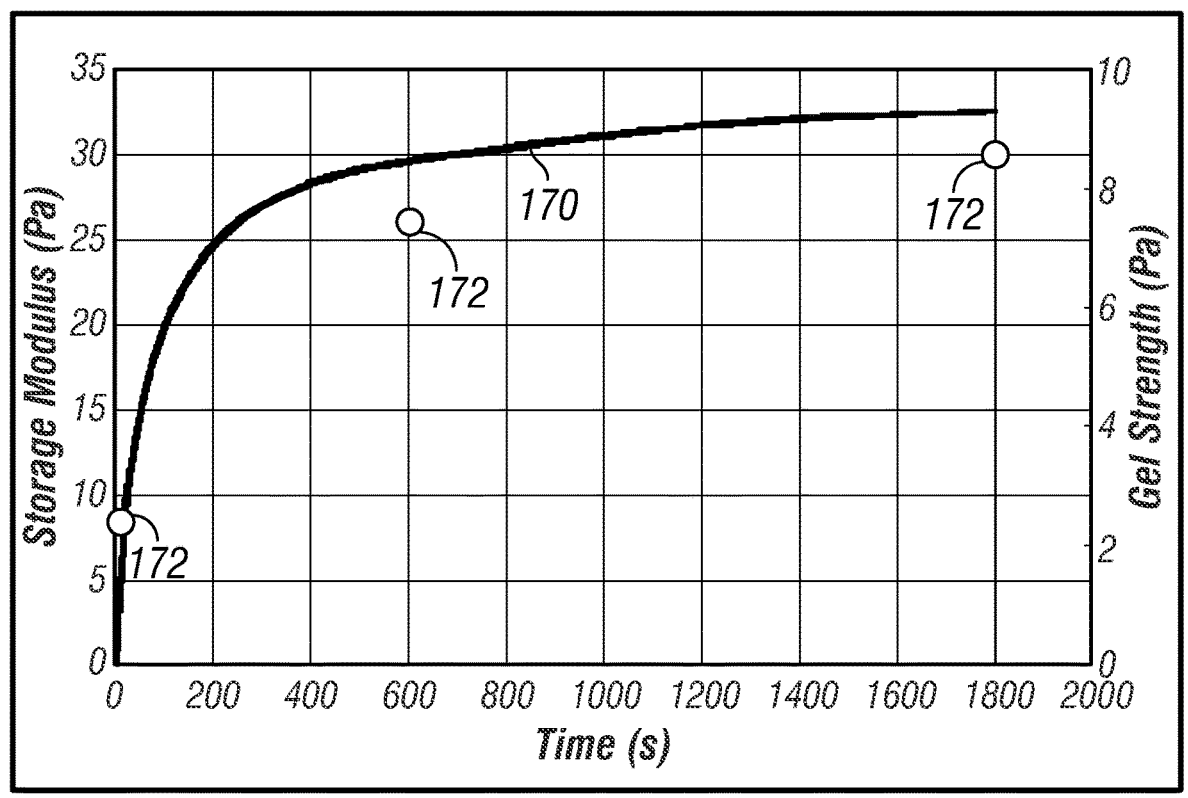
FIG. 3 is a graph of a measured storage modulus and gel strength profile of a borehole fluid.

The gel strength (GS) of the borehole fluid sample 162 is then determined by correlation from the storage modulus (G'). As an example, FIG. 3 represents a plot of a storage modulus (G') profile 170 over time from an experiment involving an oil-based-mud (OBM) with a mud weight of 13 ppg and oil-to-water ratio (OWR) of 75/25. The experiment was performed on a rotational rheometer (ANTON PAAR® MCR 501). However, the similar profile would be obtained using the setup and amplitude oscillation deformation methodology described in FIGS. 2A-C. The graph shown in FIG. 3 may be displayed on a computer display or printed on a media for viewing as a result of the measurements and determinations of the storage modulus as described above.

As shown, the storage modulus (G') can be determined continuously and in real time over the gelation period of the OBM. Although the storage modulus is a different magnitude than the gel strength, the storage modulus can capture the growth trend for the gel build-up in the OBM sample. For comparison, the gel strength measured by a single point measurement method with a FANN® 35 viscometer is also included as circles 172 in FIG. 3. The circles 172 represent measurements taken at discrete points in time as compared to the continuous monitoring from the analysis system 136 that produces the storage modulus profile 170.

Once the storage modulus profile 170 is determined, the gel strength for the borehole fluid sample 162 over the testing period of time may be determined by correlation from the storage modulus and the correlation can be made for any point in time over the testing period. The correlation of gel strength (GS) to storage modulus (G') can be made according to the following:

$$GS = \frac{G'}{\alpha} \quad \text{(Equation 6)}$$

where $\alpha$ is a factor defined as the ratio of the dynamic viscosity to the shear viscosity of the borehole fluid sample 162.

The foregoing measurements may be performed at downhole conditions, e.g., high temperature and high pressure. Therefore, the analysis system(s) 136 may include, for example, an oscilloscope to determine the phase angle $\delta$. The phase angle $\delta$ however can also be determined by analyzing the stress signal from the dynamic pressure sensor 160.

The storage modulus profile 170 may thus be used to provide more accurate gel strength information to the control system 138 for hydraulic modeling and for determining the optimal composition of the borehole fluid 122 or operation parameters for the borehole operation. For example, the gel strength may be compared with a desired gel strength and if the gel strength is outside of an acceptable range of the desired gel strength, the composition of the borehole fluid may be adjusted for the borehole operation. If the gel strength is sufficiently low, the drilling fluid may not be able to suspend solids, including weighting agents, drill cuttings, etc., especially with the drilling fluid pumps shut down. Low gel strength can also lead to problems such as pipe stick, drilling hole pack off, and accumulation of cutting beds, which is costly for cleaning up the hole. Accordingly, the composition of the borehole fluid may be altered, which, for this example, may include adding either or both of a viscosifier or an emulsifier.

Alternatively, if the gel strength is sufficiently high, high pump pressures are required to re-circulate the drilling fluid after in a static condition for a period of time. This high initiation pressure could exceed the formation gradient and cause formation fracture, and consequently, drilling fluid loss. Accordingly, the composition of the borehole fluid may be altered, which, for this example, may include solids control to remove the accumulated cutting fines. Further, for oil-based drilling fluid, base oil could be added to lower the gel strength. For water-based drilling fluid, water could be added to dilute the drilling fluid and lower the gel strength.

Further, or alternatively, a drilling parameter may be adjusted for the borehole operation. Exemplary drilling parameters may include, but are not limited to, rate of penetration, string rotary speed, weight on bit, downhole torque, surface torque, flow in, surface pressure, downhole pressure, bit orientation, bit deflection, and the like, and any combination thereof.

The analysis and results of the gel strength determination may be performed by the control system 138. Options for adjusting the borehole fluid composition or the borehole procedure parameters may also be determined based on the gel strength and displayed to a person operating the borehole operation. Alternatively, the control system 138 may use logic and machine learning techniques to implement changes to optimize the borehole operation. The borehole fluid 122 is then used or is continued to be used in the borehole operation.

Figure 4A:
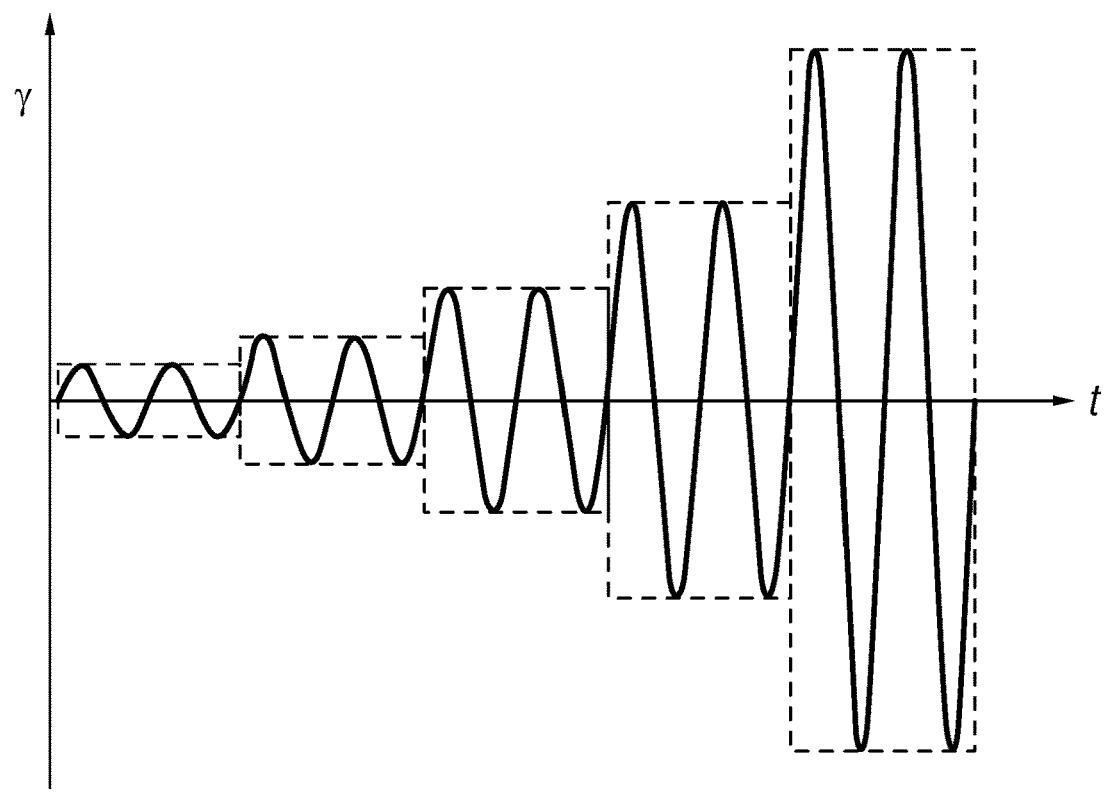
FIGS. 4A and 4B are graphs of an alternative methodology of measuring dynamic yield stress of a borehole fluid.
Figure 4B:
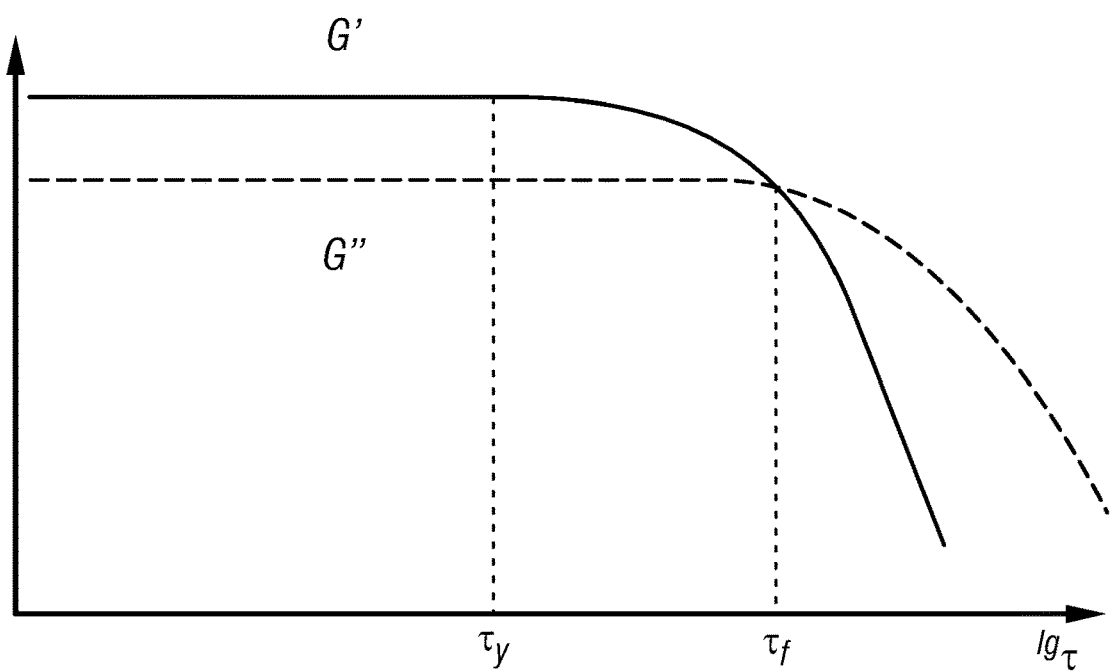

FIGS. 4A and 4B illustrate an alternative methodology of using the analysis system 136 to measure dynamic yield stress of a borehole fluid sample. As shown, the dynamic yield stress can be measured with increasing the piezo amplitude, which is controlled by a power source (not shown) of the analysis system 136. FIG. 4A shows an example of the amplitude sweep at a constant frequency to generate a force on the borehole fluid by the piezoelectric device 152. As shown in FIG. 4B, with such a force applied, the borehole fluid sample 162 will experience linear viscoelastic deformation (plateau region in FIG. 4B) until the borehole fluid sample 162 reaches the dynamic yield stress ($\tau_y$) to show significant decreasing of storage modulus. An apparent yield stress ($\tau_f$) can also be obtained when G' crossovers with G", which corresponds to the transition of the borehole fluid sample 162 from gel state to solid.

Figure 5A:
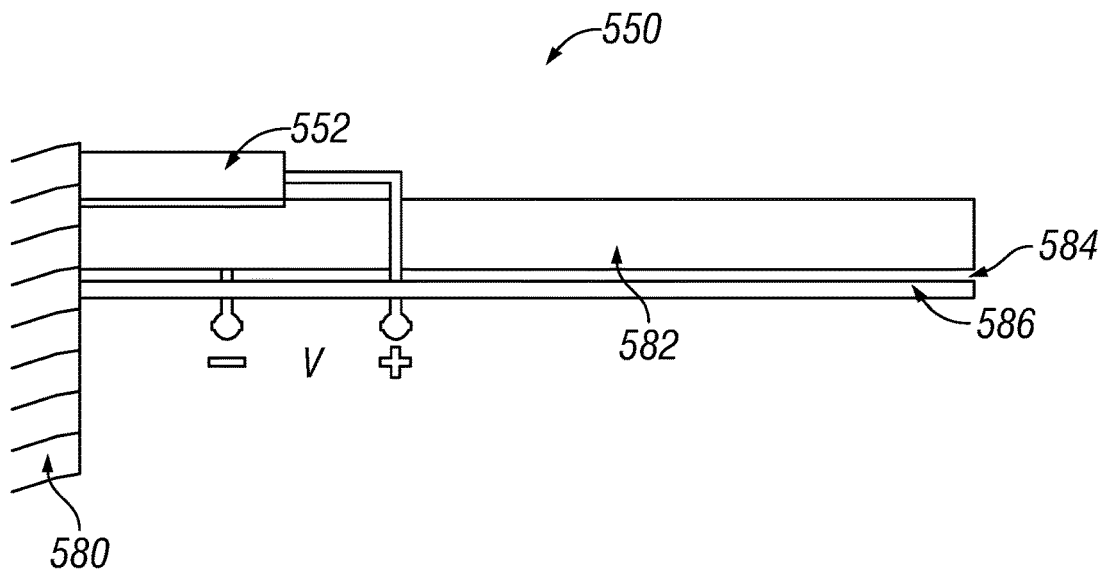
FIGS. 5A and 5B illustrates a schematic representation of a second embodiment of a rheometer of an analysis system.
Figure 5B:
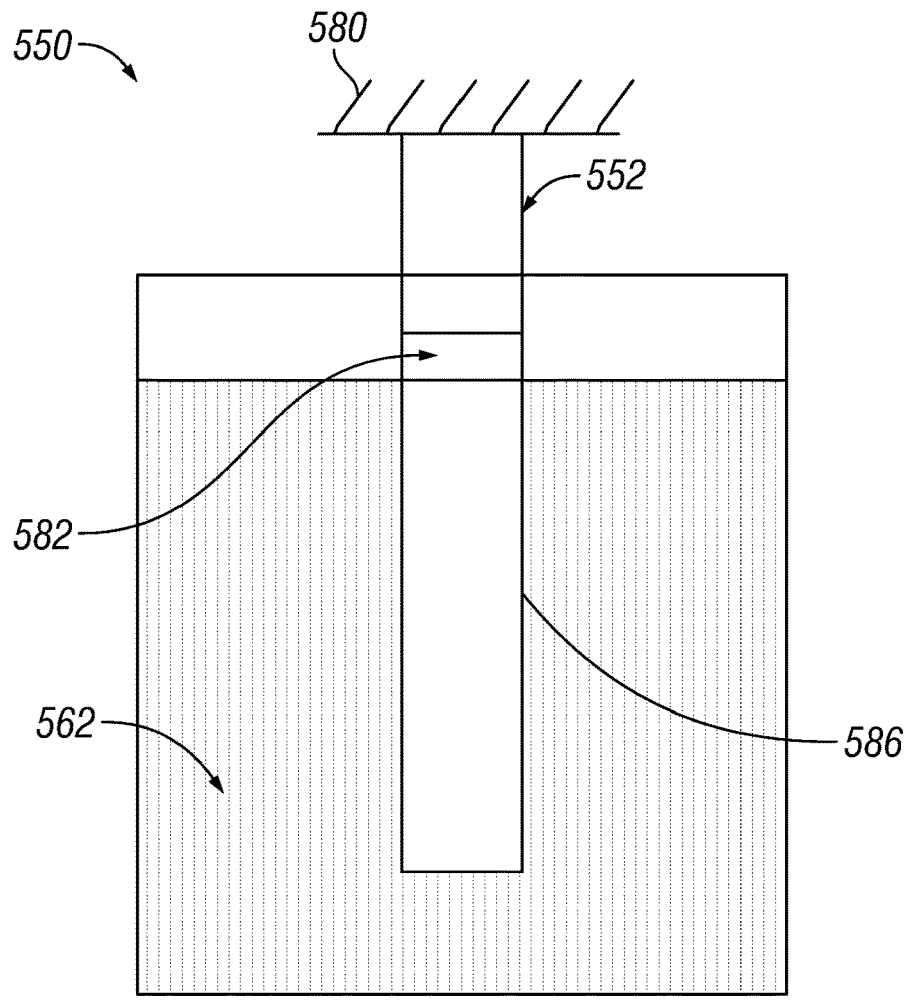

FIGS. 5A and 5B illustrate an alternative embodiment of a rheometer 550 for use with the analysis system 136. The rheometer 550 will be discussed and it is appreciated that the remaining features and functionality of the analysis system 136 discussed above also apply to the use of the rheometer 550 and therefore will not be repeated. As with the rheometer 150, the rheometer 550 is also piezoelectric-based and includes a piezoelectric device 552 anchored to an anchor 580 with electric conduits attached such that an electric current can be applied across the piezoelectric device 552. Applying an electric current across the piezoelectric device 552 causes the piezoelectric device 552 to vibrate and doing so vibrates a spring 582 in contact with the piezoelectric device 552 and also anchored at one end to the anchor 580. At least a portion of the spring 582 is submerged in the borehole fluid sample 562 so that vibrations from the spring 582 impart forces into the borehole fluid sample 562. Also at least partially submerged in the borehole fluid sample 562 is a piezoelectric sensor 586 that is also anchored to the anchor 580 at one end and separated from the spring by a gap 584. The gap 584 is wide enough so that borehole fluid sample 562 can flow between the spring 582 and the piezoelectric sensor 586 and not so wide that the piezoelectric sensor 586 cannot detect forces imparted to the borehole fluid sample 562 from the spring 582. For example, the gap 584 may range, from about 0.1 mm to about 2 mm, depending on the resolution of the piezoelectric sensor 586. As shown, the piezoelectric sensor 586 extends parallel and along one side of the spring 582 and is the same length as the spring 582. However, the piezoelectric sensor 586 may be any suitable shape and in any suitable position for detecting forces imparted into the borehole fluid sample 562 from the spring 582.

Operationally, a voltage is applied across the piezoelectric device 552 to cause the piezoelectric device 552 to vibrate, which in turn causes the spring 582 to vibrate based on the voltage applied. At least a portion of the spring 582 is submerged in the borehole fluid sample 562 and the vibrations of the spring 582 impart forces into the borehole fluid sample 562. The piezoelectric sensor 586 is close enough that the force response in the borehole fluid sample 562 imparts forces onto the piezoelectric sensor 586 that can be measured by monitoring an electric current produced by the changes in shape of the piezoelectric sensor 586 based on the forces in the borehole fluid sample 562. As with the analysis system 136, the measured force is then used to determine the storage modulus of the borehole fluid sample 562 as described above. The gel strength can then be correlated to the storage modulus over the testing time as described above.

One or more specific embodiments of the systems and methods for borehole fluid gel strength measurement have been described. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure.

Reference throughout this specification to "one embodiment," "an embodiment," "an embodiment," "embodiments," "some embodiments," "certain embodiments," or similar language means that a particular feature, structure, or characteristic described in connection with the embodiment may be included in at least one embodiment of the present disclosure. Thus, these phrases or similar language throughout this specification may, but do not necessarily, all refer to the same embodiment.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the disclosed embodiments. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps.

The embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

Certain embodiments of the disclosure may include a method of performing a borehole operation with a borehole fluid that includes applying an amplitude oscillation deformation force to a sample of the borehole fluid over a period of time, measuring the deformation force from the sample, determining a storage modulus of the borehole fluid over the period of time based on the measured deformation force, determining a gel strength of the borehole fluid by correlation with the storage modulus, comparing the gel strength with a desired gel strength and if the gel strength is outside of an acceptable range of the desired gel strength, adjusting a drilling parameter, a composition of the borehole fluid, or a combination thereof, and using the borehole fluid in the borehole operation.

The embodiments of any preceding paragraph or combination thereof and further including applying the amplitude oscillation deformation force to the borehole fluid continuously over the period of time.

The embodiments of any preceding paragraph or combination thereof, where the period of time comprises a gelation period for the borehole fluid.

The embodiments of any preceding paragraph or combination thereof, where applying an amplitude oscillation deformation force to the borehole fluid comprises imparting a force using a piezoelectric device.

The embodiments of any preceding paragraph or combination thereof, where applying an amplitude oscillation deformation force to the borehole fluid comprises maintaining a frequency and amplitude of the oscillation deformation force over the period of time.

The embodiments of any preceding paragraph or combination thereof, where applying an amplitude oscillation deformation force to the borehole fluid further comprises adjusting an amplitude while maintaining a frequency and determining a dynamic yield stress of the borehole fluid based on when the borehole fluid sample transitions from linear viscoelastic deformation to dynamic yield stress.

The embodiments of any preceding paragraph or combination thereof, where the borehole fluid comprises drilling fluid and the borehole operation comprises drilling a borehole.

Certain embodiments of the disclosure may include an apparatus for evaluating the gel strength of a borehole fluid for use in a borehole operation, including a piezoelectric device operable to apply an amplitude oscillation deformation force to a sample of the borehole fluid over a period of time, a sensor operable to measure the deformation force from the sample of the borehole fluid, and a processor. The processor is operable to determine a storage modulus of the borehole fluid over time based on the measured deformation force, determine a gel strength of the borehole fluid by correlation with the storage modulus, and compare the gel strength with a desired gel strength to determine if the gel strength is with an acceptable range of a desired gel strength.

The embodiments of any preceding paragraph or combination thereof, where the piezoelectric device is operable to apply the amplitude oscillation deformation force to the borehole fluid continuously over the period of time.

The embodiments of any preceding paragraph or combination thereof, where the period of time comprises a gelation period for the borehole fluid.

The embodiments of any preceding paragraph or combination thereof, where the piezoelectric device is operable to apply the amplitude oscillation deformation force by imparting force to a spring and the sensor comprises a piezoelectric sensor.

The embodiments of any preceding paragraph or combination thereof, where the piezoelectric device is operable to apply the amplitude oscillation deformation force to the sample of the borehole fluid by maintaining a frequency and amplitude of the oscillation deformation force over the period of time.

The embodiments of any preceding paragraph or combination thereof, where the piezoelectric device is operable to apply the amplitude oscillation deformation force to the borehole fluid sample by adjusting an amplitude of the deformation force while maintaining a frequency until the sample transitions from linear viscoelastic deformation to dynamic yield stress and where the processor is operable to determine the dynamic yield stress of the borehole fluid sample based on the transition.

The embodiments of any preceding paragraph or combination thereof, where the sample of the borehole fluid comprises drilling fluid and the borehole operation comprises drilling a borehole.

Certain embodiments of the disclosure may include a method of determining the gel strength of a fluid that includes applying an amplitude oscillation deformation force to the fluid over a period of time, measuring the deformation force from the fluid over the period of time, determining a storage modulus of the fluid over the period of time based on the measured deformation force, and determining a gel strength of the fluid by correlation with the storage modulus.

The embodiments of any preceding paragraph or combination thereof, further comprising applying the amplitude oscillation deformation force to the fluid continuously over the period of time.

The embodiments of any preceding paragraph or combination thereof, where the period of time comprises a gelation period for the fluid.

The embodiments of any preceding paragraph or combination thereof, where applying an amplitude oscillation deformation force to the fluid comprises imparting a force using a piezoelectric device.

The embodiments of any preceding paragraph or combination thereof, where applying an amplitude oscillation deformation force to the fluid comprises maintaining a frequency and amplitude of the oscillation deformation force over the period of time.

The embodiments of any preceding paragraph or combination thereof, where applying an amplitude oscillation deformation force to the fluid further comprises adjusting an amplitude while maintaining a frequency and determining a dynamic yield stress of the fluid based on when the fluid sample transitions from linear viscoelastic deformation to dynamic yield stress.

What is claimed is:

1. A method of performing a borehole operation with a borehole fluid comprising:
    applying an amplitude oscillation deformation force to a sample of the borehole fluid over a period of time;
    measuring the deformation force from the sample;
    determining a storage modulus of the borehole fluid over the period of time based on the measured deformation force;
    determining a gel strength of the borehole fluid by correlation with the storage modulus;
    comparing the gel strength with a selected gel strength for performing the borehole operation and if the gel strength is outside of a range with respect to the selected gel strength for performing the borehole operation, adjusting a drilling parameter, a composition of the borehole fluid, or a combination thereof; and
    using the borehole fluid in the borehole operation.

2. The method of claim 1, further comprising applying the amplitude oscillation deformation force to the borehole fluid continuously over the period of time.

3. The method of claim 1, where the period of time comprises a gelation period for the borehole fluid.

4. The method of claim 1, where applying an amplitude oscillation deformation force to the borehole fluid comprises imparting a force using a piezoelectric device.

5. The method of claim 1, where applying an amplitude oscillation deformation force to the borehole fluid comprises maintaining a frequency and amplitude of the oscillation deformation force over the period of time.

6. The method of claim 1, where applying an amplitude oscillation deformation force to the borehole fluid further comprises adjusting an amplitude while maintaining a frequency and determining a dynamic yield stress of the borehole fluid based on when the borehole fluid sample transitions from linear viscoelastic deformation to dynamic yield stress.

7. The method of claim 1, where the borehole fluid comprises drilling fluid and the borehole operation comprises drilling a borehole.

8. An apparatus for evaluating the gel strength of a borehole fluid for use in a borehole operation, comprising:
   a piezoelectric device operable to apply an amplitude oscillation deformation force to a sample of the borehole fluid over a period of time;
   a sensor operable to measure the deformation force from the sample of the borehole fluid; and
   a processor operable to:
      determine a storage modulus of the borehole fluid over time based on the measured deformation force;
      determine a gel strength of the borehole fluid by correlation with the storage modulus; and
      compare the gel strength with a selected gel strength for performing the borehole operation to determine if the gel strength is within a range with respect to the selected gel strength for performing the borehole operation.

9. The apparatus of claim 8, where the piezoelectric device is operable to apply the amplitude oscillation deformation force to the borehole fluid continuously over the period of time.

10. The apparatus of claim 8, where the period of time comprises a gelation period for the borehole fluid.

11. The apparatus of claim 8, where the piezoelectric device is operable to apply the amplitude oscillation deformation force by imparting force to a spring and the sensor comprises a piezoelectric sensor.

12. The apparatus of claim 8, where the piezoelectric device is operable to apply the amplitude oscillation deformation force to the sample of the borehole fluid by maintaining a frequency and amplitude of the oscillation deformation force over the period of time.

13. The apparatus of claim 8, where the piezoelectric device is operable to apply the amplitude oscillation deformation force to the borehole fluid sample by adjusting an amplitude of the deformation force while maintaining a frequency until the sample transitions from linear viscoelastic deformation to dynamic yield stress and where the processor is operable to determine the dynamic yield stress of the borehole fluid sample based on the transition.

14. The apparatus of claim 8, where the sample of the borehole fluid comprises drilling fluid and the borehole operation comprises drilling a borehole.

15. A method of determining the gel strength of a fluid comprising:
   applying a linear amplitude oscillation deformation force to the fluid in a normal direction relative to the fluid over a period of time;
   measuring the deformation force from the fluid continuously over the period of time using a dynamic pressure sensor on the opposite side of the fluid from the force being applied;
   determining a storage modulus of the fluid continuously over the period of time based on the measured deformation force to produce a storage modulus profile; and
   determining a gel strength of the fluid by correlation with the storage modulus profile based on a ratio of a dynamic viscosity of the fluid to a shear viscosity of the fluid.

16. The method of claim 15, further comprising applying the linear amplitude oscillation deformation force to the fluid continuously over the period of time.

17. The method of claim 15, where the period of time comprises a gelation period for the fluid.

18. The method of claim 15, where applying the linear amplitude oscillation deformation force to the fluid comprises imparting a force using a piezoelectric device.

19. The method of claim 15, where applying the linear amplitude oscillation deformation force to the fluid comprises maintaining a frequency and amplitude of the oscillation deformation force over the period of time.

20. The method of claim 15, where applying the linear amplitude oscillation deformation force to the fluid further comprises adjusting an amplitude while maintaining a frequency and determining a dynamic yield stress of the fluid based on when the fluid sample transitions from linear viscoelastic deformation to dynamic yield stress.

\* \* \* \* \*